US008737711B2

(12) United States Patent
Goto et al.

(10) Patent No.: US 8,737,711 B2
(45) Date of Patent: May 27, 2014

(54) X-RAY CT IMAGE FORMING METHOD AND X-RAY CT APPARATUS USING THE SAME

(75) Inventors: Taiga Goto, Tokyo (JP); Yoshiaki Sugaya, Tokyo (JP); Koichi Hirokawa, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 518 days.

(21) Appl. No.: 13/056,830

(22) PCT Filed: Jul. 30, 2009

(86) PCT No.: PCT/JP2009/063583
§ 371 (c)(1),
(2), (4) Date: Jan. 31, 2011

(87) PCT Pub. No.: WO2010/016425
PCT Pub. Date: Feb. 11, 2010

(65) Prior Publication Data
US 2011/0135182 A1   Jun. 9, 2011

(30) Foreign Application Priority Data
Aug. 7, 2008   (JP) .................................. 2008-203839

(51) Int. Cl.
*G06K 9/00*   (2006.01)
(52) U.S. Cl.
USPC ......................................................... 382/131
(58) Field of Classification Search
USPC .................................. 382/128–132; 600/425
See application file for complete search history.

(56) References Cited

U.S. PATENT DOCUMENTS

| 2004/0146126 A1* | 7/2004  | Wheatley et al. ............. 375/343 |
| 2004/0146136 A1  | 7/2004  | Gringauz et al. |
| 2005/0100203 A1* | 5/2005  | Fujisawa ....................... 382/130 |
| 2009/0324044 A1* | 12/2009 | Grasruck et al. .............. 382/131 |

FOREIGN PATENT DOCUMENTS

| JP | 5-237089   | 9/1993 |
| JP | 9-253079   | 9/1997 |
| JP | 2004-528100 | 9/2004 |

OTHER PUBLICATIONS

International Search Report in PCT/JP2009/063583.

* cited by examiner

*Primary Examiner* — Amara Abdi
(74) *Attorney, Agent, or Firm* — Cooper & Dunham LLP

(57) ABSTRACT

In order to provide a CT image forming method that can reduce an artifact caused by an image reconstructing method, and an X-ray CT apparatus using the same, an X-ray CT image forming method according to the invention is characterized in that an artifact component caused by the image reconstructing method of the projection data is obtained by calculation; the determined artifact component is subtracted from the projection data to create corrected projection data containing an inverted artifact component, and image reconstruction is executed on the corrected projection data to obtain a reconstructed image from which the artifact is reduced. The inverted artifact component is obtained as differential between the projection data and re-projection data obtained by inversely projecting a reconstructed image which is obtained by reconstructing the projection data concerned.

9 Claims, 8 Drawing Sheets

X-RAY CT IMAGE FORMING METHOD AND X-RAY CT APPARATUS USING THE SAME

TECHNICAL FIELD

The present invention relates to an X-ray CT image forming method and an X-ray CT apparatus using the same, and particularly to a technique for reducing artifact caused by an image reconstructing method of projection data obtained by CT scan.

BACKGROUND ART

An X-ray CT image is obtained by executing image reconstruction on projection data comprising plural view data which are obtained by performing CT scan based on an X-ray tube and an X-ray detector around an examinee. A false image called an artifact may occur in a reconstructed CT image due to various causes. When an artifact occurs on an image, it disturbs doctor's image diagnosis, and thus an artifact reducing technique corresponding to the type of an artifact has bee developed.

Recently, a multi-slice type X-ray CT apparatus (hereinafter referred to as multi-slice CT) in which plural arrays of detection elements of an X-ray detector are arranged in a body axis direction of an examinee has been popular, and the number of element arrays of the detector has increased. The multi-slice CT can image a broader examinee area by one scan as compared with conventional single slice CT, and thus it brings a great merit that the examination time is shortened. The shortening of the examination time is proportional to the number of the detection element arrays for the same scan speed and the same detection element size. Therefore, the detection element arrays multiply in power of 2, and a multi-slice CT equipped with a detector having 64 arrays of detection elements has been recently sold in the market.

The image reconstructing method of the X-ray CT apparatus is roughly classified into an analytic reconstruction method and an algebraic reconstruction method. The analytic reconstruction method of the image reconstructing method contains a Fourier transform method, a filtered back projection method and a convolution integral method, and the algebraic reconstruction method contains a successive approximation reconstruction method represented by MLEM (Maximum Likelihood Expectation Maximization) method or OSEM (Ordered Subset Expectation Maximization) method. When the analytic method which has been practically used at present is applied to a multi-slice CT having a broad cone angle, it has a problem that a cone beam artifact occurs due to incompleteness of a reconstruction algorithm. On the other hand, the algebraic method is known as having higher completeness than the analytic method, however, it has a problem that a very long calculation time is required because recursive calculation is executed. Therefore, the algebraic method has been hitherto used in a nuclear medicine field, however, it has not been popular in an X-ray CT field. However, the problem that the calculation time of the successive approximation reconstruction method is long has been solved by the recent development of the computer technology, and Patent Document 1 discloses that image formation of an X-ray CT apparatus is performed by using the successive approximation reconstruction method to improve the image quality.

Various methods belonging to the analytic method have been considered as the image reconstructing method of the multi-slice CT at present. With respect to a multi-slice CT having a device with a small number of detection element arrays, for example, four arrays of detection elements, a filtered back projection (Filtered Back Projection) method for a conventional single slice CT can be applied. However, with respect to the larger number of detection elements, for example, a multi-slice CT having 64 arrays of detection elements, adoption of an image reconstructing method called a Feldkamp (Feldkamp) method disclosed in non-patent document 1 or an image reconstructing method corresponding to an improved Feldkamp method has been considered.

The Feldkamp method is an approximation image reconstructing method based on the filtered back projection method. In this method, an effect of an incident angle (cone angle) of X-ray flux (cone beam X-ray) emitted from an X-ray tube to an X-ray detector on the detection element arrays at the end portions is considered, and it is said that occurrence of a cone beam artifact inherent to the multi-slice CT is relatively less.

PRIOR ART DOCUMENT

Patent Document

Patent Document 1: JP-A-2006-25868

Non-Patent Document

Non-patent Document 1: L. A. Feldkamp et al. Practical conebeam algorithm, J. Opt. Soc. Am. A, Vol 1, No. 6, pp 612-619, 1984

SUMMARY OF THE INVENTION

Problem to be Solved by the Invention

It is considered that the cone beam artifact can be suppressed, however, it is impossible to completely extinguish the cone beam artifact even by the Feldkamp method or the improved method thereof. Furthermore, from the viewpoint of a technological trend that the detection element arrays of the multi-slice CT further multiply, it has been required to establish a technique of reducing the cone beam artifact.

The invention has been implemented in view of the foregoing technical background, and has an object to provide a CT image forming method that can reduce an artifact caused by an image reconstructing method, and an X-ray CT apparatus using the CT image forming method.

Means of Solving the Problem

In order to solve the above problem, according to the invention, an X-ray CT image forming method that obtains a reconstructed image of an examination site of an examinee by executing image reconstruction on projection data obtained by CT scan is characterized in that an artifact component caused by the image reconstructing method of the projection data is obtained by calculation; the determined artifact component is subtracted from the projection data to create corrected projection data containing an inverted artifact component, and image reconstruction is executed on the corrected projection data to obtain a reconstructed image from which the artifact is reduced. The inverted artifact component is obtained as differential data between the projection data and re-projection data obtained by re-projecting a reconstructed image which is obtained by reconstructing the projection data concerned.

Furthermore, in order to solve the foregoing problem, an X-ray CT image forming method that obtains a reconstructed image of an examination site of an examinee by executing image reconstruction on projection data obtained by CT scan is characterized by comprising:

(1) a step of executing image reconstruction on the projection data to obtain an initial reconstructed image;

(2) a step of re-projecting the initial reconstructed image to obtain re-projection data;

(3) a step of obtaining differential data between the projection data and the re-projection data;

(4) a step of subtracting the differential data from the projection data to obtain corrected projection data containing an inverted artifact component; and (5) a step of executing image reconstruction on the corrected projection data to obtain a corrected reconstructed image.

It is further characterized that subsequently to the step (5), the initial reconstructed image of the step (2) is replaced by the corrected reconstructed image obtained in the step (5), and the steps from (2) to (5) are repeated at n times (n represents an integer of n≥1, and the upper limit thereof is determined).

Furthermore, in order to solve the foregoing problem, an X-ray CT apparatus in which an X-ray source and an X-ray detector are disposed to face each other and sandwich an examinee therebetween and projection data obtained by executing CT scan on the examinee are reconstructed by an image processing device to obtain a reconstructed image of an examination site of the examinee is characterized in that the image processing device comprises: artifact component extracting means that extracts an artifact component caused by an image reconstructing method of the projection data; corrected projection data creating means that subtracts the artifact component from the projection data to create corrected projection data containing an inverted artifact component; and corrected reconstructed image creating means that executes image reconstruction on the corrected projection data to create a corrected reconstructed image from which the artifact caused by the image reconstructing method is reduced. The artifact component extracting means is characterized by comprising: means that re-projects the reconstructed image obtained by reconstructing the projection data to obtain re-projection data, and means that obtains differential data between the projection data and the re-projection data.

Furthermore, the image processing device is characterized by comprising successive approximation image reconstructing means that makes the artifact component extracting means re-project the corrected reconstructed image created by the corrected reconstructed image creating means again to obtain n-th re-projection data and then obtain n-th differential data between the projection data and the n-th differential data, makes the corrected projection data creating means subtract the n-th differential data from the projection data to obtain n-th corrected projection data, and makes the corrected reconstructed image creating means repetitively execute an operation of reconstructing the n-th corrected projection data from n=1 till n=n wherein n represents an integer to obtain a corrected reconstructed image in which the artifact diminishes gradually.

It is desired that an upper limit value of the repeat frequency n is set before image reconstruction processing, or it is desired that input means for inputting repetition of obtaining the corrected reconstructed image on a case-by-case basis is provided to an operation unit.

It is desired that the invention is applied to an X-ray CT apparatus that has a multi-slice type X-ray detector as the X-ray detector and uses a method belonging to a filtered back projection method as the image reconstructing method to perform image reconstruction.

Effect of the Invention

According to the invention, an artifact caused by the image reconstructing method in the X-ray CT apparatus can be reduced.

BEST MODE FOR CARRYING OUT THE INVENTION

Preferred embodiments according to the invention will be described in detail with reference to FIGS. 1 to 8.

Figure 1:
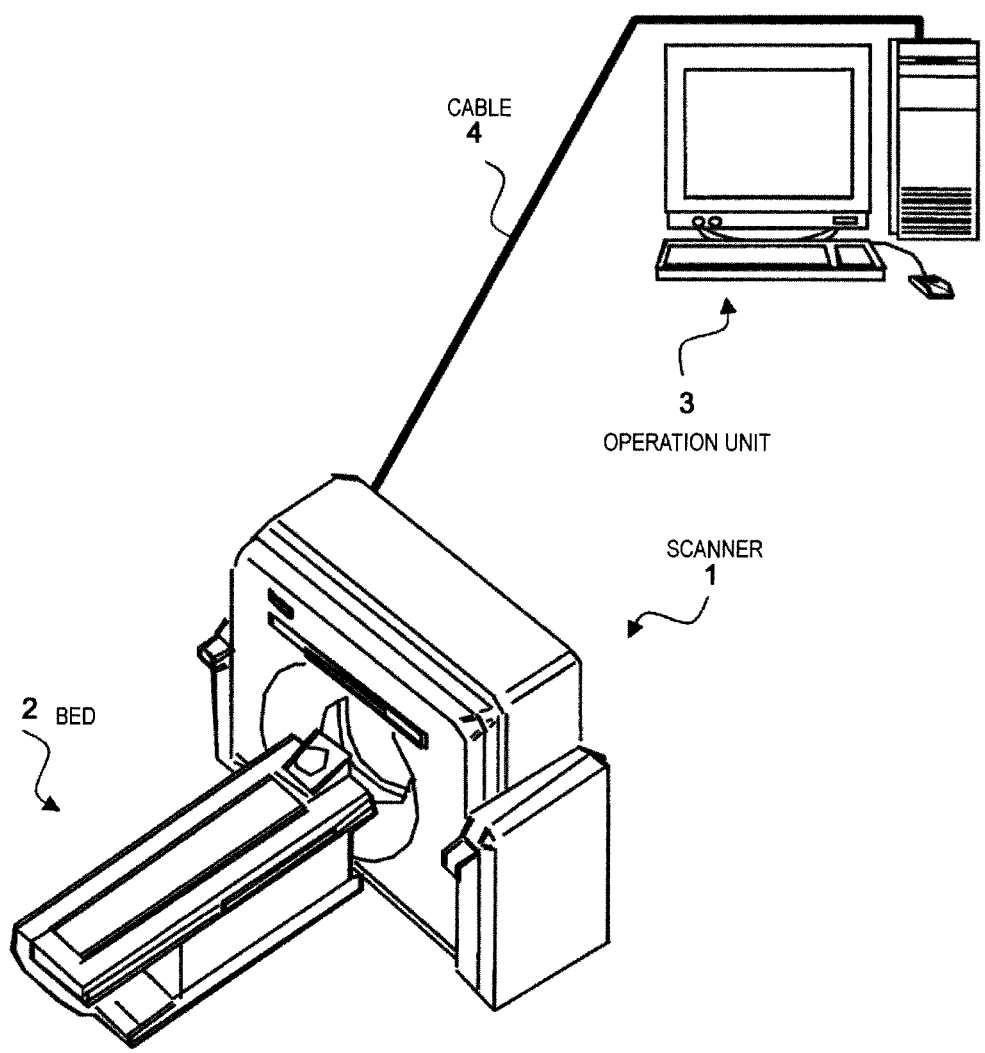
[FIG. 1] is a perspective view showing the overall construction of an X-ray CT apparatus.

As shown in FIG. 1, a multi-slice CT according to a first embodiment has a scanner 1, a bed 2 and an operation unit 3 connected to the scanner 2 through a cable 4. The scanner 1 serves to rotate an X-ray tube and an X-ray detector around an examinee 24 while emitting X-ray and measure an X-ray absorption coefficient of a tissue constituting the examinee from many directions. The bed 2 serves to feed in/out the examinee 24 into/from an opening portion of the scanner 1. The operation unit 3 has an input device for inputting imaging parameters and reconstructing parameters, a processing device for processing data output from the X-ray detector and a display device for displaying a reconstructed image and incidental information thereof.

Figure 2:
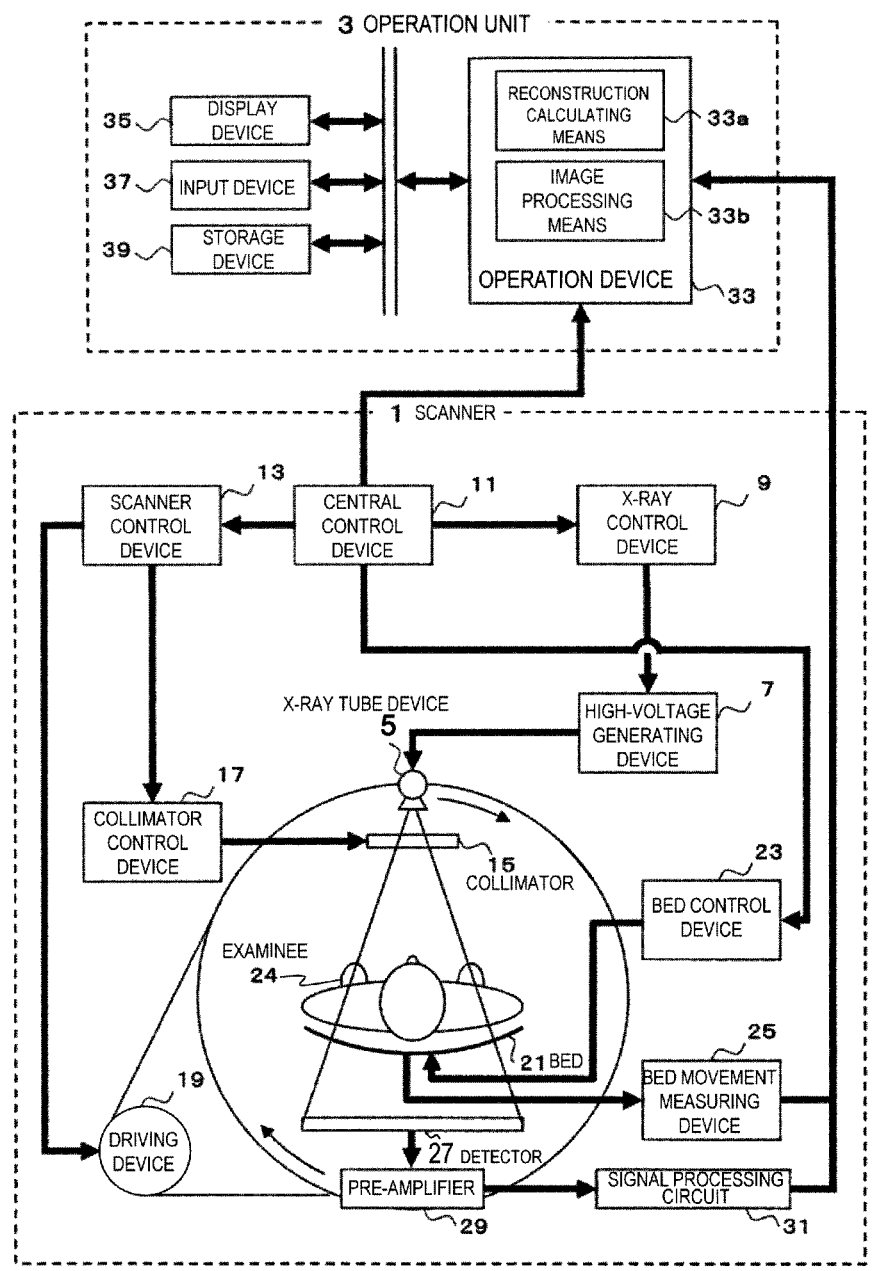
[FIG. 2] is a block diagram showing the detailed construction of the X-ray CT apparatus according to the invention.

FIG. 2 is a block diagram showing the construction of a multi-slice CT according to the invention. The scanner 1 has an X-ray tube device 5 as an X-ray generating source, a high-voltage generating device 7, an X-ray control device 9, a central control device (CPU) 11, a scanner control device 13, a collimator 15, a collimator control device 17, a scanner rotational driving device 19, an X-ray detector 27, a pre-amplifier 29, a signal processing circuit 31, etc. The X-ray detector 27 has not only an array of X-ray detection elements arranged in an arc direction of a predetermined radius around the focus point of the X-ray tube (hereinafter referred to as a channel direction), but also plural arrays of X-ray detection elements in a cross-sectional plane direction (hereinafter referred to as a slice direction) of the examinee.

The bed 2 comprises a top plate 21, a bed control device 23, a bed movement measuring device 25, etc.

The operation unit 3 has an operation device 33, a display device 35 comprising CRT or a liquid crystal display, an input device 37 such as a keyboard and a mouse, and a storage device 39.

In the thus-constructed multi-slice CT, when an X-ray imaging condition (tube voltage, tube current, bed moving speed, slice pitch, etc.) and reconstruction parameters (FOV, reconstructed image size, back projection phase width, reconstruction filter function, etc.) are input from an input device 37 of the operation unit 3 by an operator, control signals necessary for imaging are transmitted from CPU 11 to the X-ray control device 9, the bed control device 23, the scanner control device 13, the scanner rotational driving device 19 and the collimator control device 17. Subsequently, when the operator inputs an imaging start instruction to the operation unit 3, a control signal is transmitted from CPU 11 to the scanner rotational driving device 19, and the X-ray tube device 5 and the X-ray detector 27 are started to rotate around the examinee 24. The rotation concerned reaches a steady speed, and an imaging start signal is emitted from the scanner rotational driving device 19 at a timing at which the X-ray tube device 5 comes to a predetermined rotational angle position.

When the imaging start signal is issued, an X-ray radiation start signal is output from CPU 11 to the X-ray control device 9, a control signal is transmitted from the X-ray control device 9 to the high-voltage generating device 7, a set tube voltage is applied to the X-ray tube device 5, tube current is supplied to a cathode filament of the X-ray tube device 5, and the examinee 24 is irradiated with X-ray from the X-ray tube device 5.

Furthermore, a signal concerning the movement of the examinee under scanning is input from CPU 11 to the bed control device 23, and the top plate 21 on which the examinee 24 is put is set to any one state of a stationary state, a step feeding operation state and a continuous moving operation state in accordance with the signal concerned.

X-ray emitted from the X-ray tube device 5 is irradiated to a tissue of the examinee in an X-ray irradiation field which is set by the collimator 15, attenuated in accordance with the X-ray absorption coefficient of the tissue of the examinee 24, and detected by the X-ray detector 27. The X-ray detected by the X-ray detector 27 is converted to current, amplified by the pre-amplifier 29, subjected to A/D conversion, logarithmic conversion, calibration processing, etc. in the signal processing circuit 31, and then input as view data into the operation device 33 of the operation unit 3. This view data are obtained every predetermined rotational angle of the X-ray tube device 5 and the X-ray detector 27, and successively taken into the operation device 33.

When a predetermined number of view data (projection data) which are required to reconstruct a CT image are taken into the operation device 33, an image reconstructing calculation is performed by reconstruction calculating means 33a in the operation device 33 to form a reconstructed image. The reconstructed image is saved into the storage device 39 in the operation unit 3, subjected to image processing in the image processing means 33b as occasion demands, and then displayed as a CT image on the display device 35.

FIRST EMBODIMENT

Figure 3:
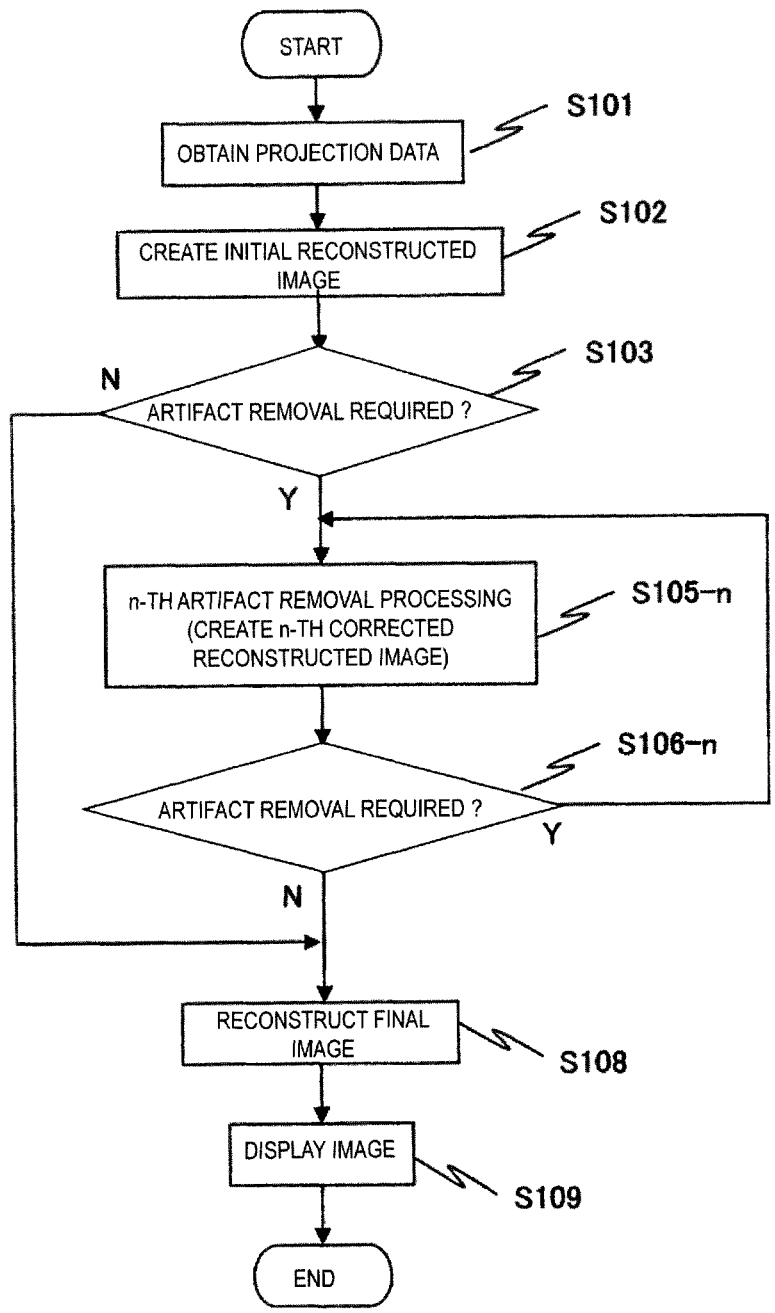
[FIG. 3] is a flowchart showing the processing procedure of CT image formation according to a first embodiment of the invention.
Figure 4:
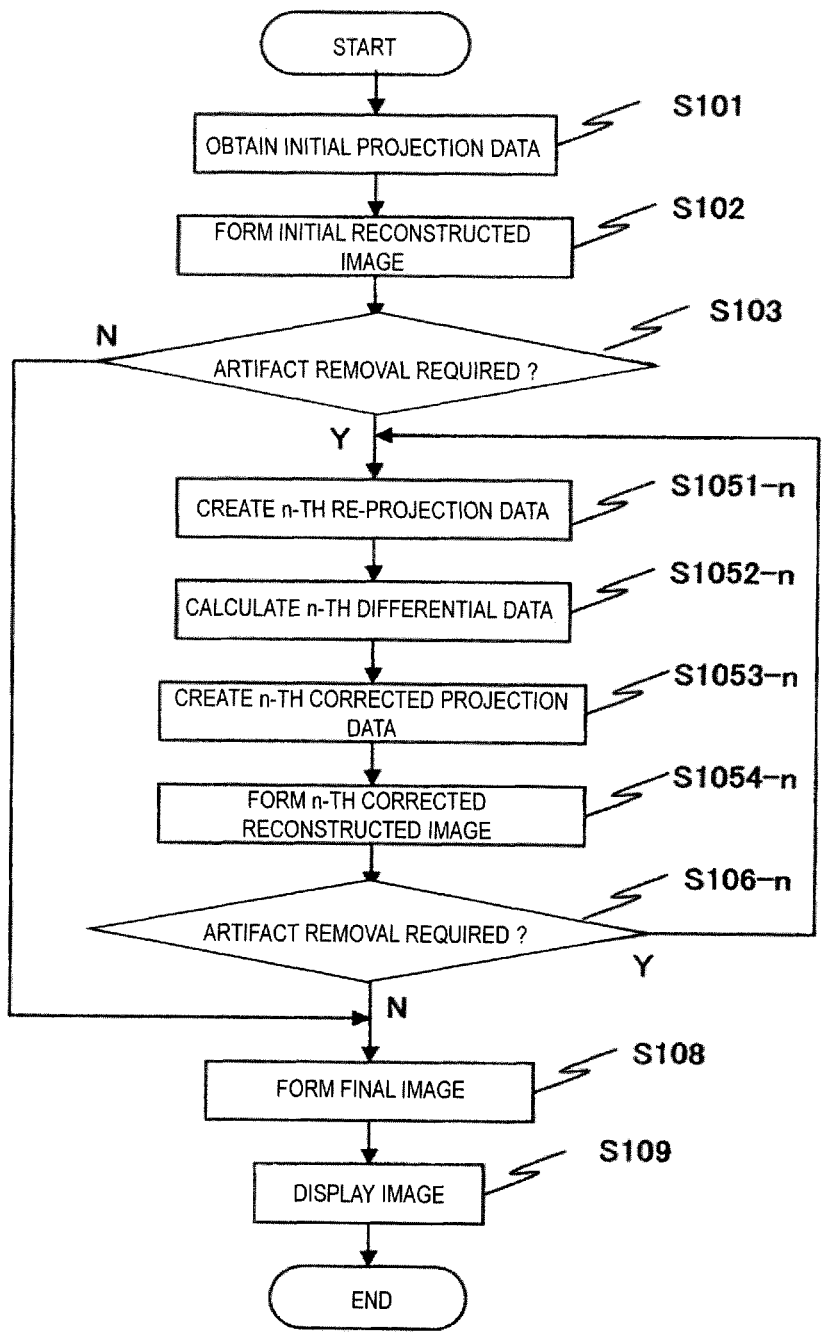
[FIG. 4] is a flowchart showing the processing procedure of the CT image formation according to the first embodiment of the invention.

Next, a first embodiment of the CT image forming method according to the invention will be described with reference to FIGS. 3 to 5.

Figure 5:
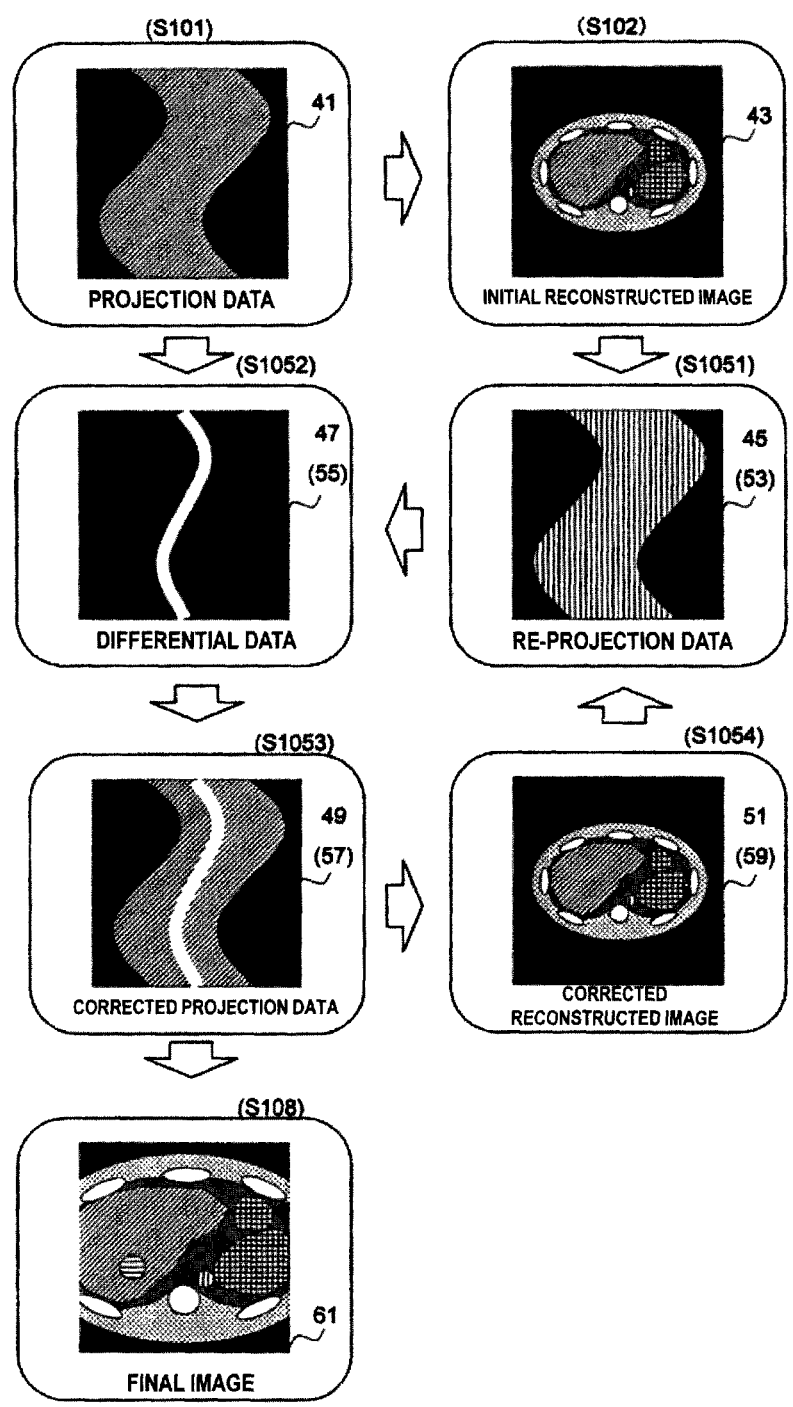
[FIG. 5] is a diagram showing a graphed flowchart of FIG. 3.

First, the examinee 24 is subjected to imaging (CT scan) by the CT apparatus to obtain initial projection data 41 shown in FIG. 5, and the initial projection data 41 are taken into the operation device 33 (step 101). The initial projection data 41 shown in FIG. 5 are shown as a pair of projection data by sinograms, however, plural pairs of projection data are taken into the operation device 33.

The initial projection data 41 taken into the operation device 33 are subjected to image reconstruction calculation based on the three-dimensional filtered back projection method, for example, the Feldkamp method by the reconstruction calculating means 33a in the operation device 33, thereby forming an initial reconstructed image 43 (step 102). This initial reconstructed image 43 is also shown as one image in FIG. 5, however, images whose number corresponds to the initialized number of slices are reconstructed. These initial reconstructed images 43 are displayed on the display device 35. The above operation is well known in the multi-slice CT, and thus the detailed description thereof is omitted.

An operator successively observes the initial reconstructed images 43 displayed on the display device 35, and determines whether an image of a site to be diagnosed can be supplied for diagnosis, that is, determines whether an artifact is required to be removed or not (step 103). When the operator determines that many artifacts caused by the image reconstructing method exist on the image and thus there is a risk that they pose a problem for the diagnosis (Y (Yes) of step 103), a removal processing operation of the artifacts based on successive approximation processing of the step S105 and subsequent steps is executed. Furthermore, When the operator determines that the artifacts do not pose any problem for the diagnosis (N (No) of step 103), the successive approximation processing of the step 105 and subsequent steps is not executed, and an operation of creating a final reconstructed image described later is executed. The determination result concerning whether the processing of removing the artifacts is necessary or not may be input to a window provided on the screen of the display device 35 through the input device 37 by the operator.

When the operator inputs the necessity of the removal processing of the artifacts, CPU 11 makes the operation device 33 execute first artifact removal processing (step 105-n) (n represents a repeat frequency, and in this case, n=1. Accordingly, step 105-1 is described. The same is applied below). The operation device 33 which receives an instruction of executing the first artifact removal processing from CPU 11 re-projects the initial reconstructed image 43 along an X-ray beam or along a scan trajectory. Accordingly, n-th re-projection data (in this case, n=1, and it is the first re-projection data. The same is applied below.) 45 is created (step 1051-n) (in this case, n–1, and thus step 1051-1 is described. The same is applied below). This re-projection may be executed on all the initial reconstructed images, or may be executed on only images for which the operator determines that many artifacts exist on the images and thus pose a problem for diagnosis. The first re-projection data 45 created by the above re-projection contains an artifact component caused by the image reconstructing method.

When the first re-projection data 45 is created, the operation device 33 executes the differential calculation of the initial projection data 41 and the first re-projection data 45 on the basis of an instruction of CPU 11 to obtain n-th differential data (in this case, n=1 and thus it is the first differential data. The same is applied below.) 47 (step 1052-1). This first differential data 47 is an artifact component caused by the image reconstructing method. The differential calculation may be executed on all the initial projection data 41 and the first re-projection data 45. However, the differential calculation may be executed on a pair of a part of the initial projection data 41 and the corresponding first re-projection data, the execution of the differential calculation on the pairs of the other initial projection data 41 and the corresponding first re-projection data may be omitted, and they may be determined by weighting processing corresponding to an X-ray incident angle of the projection data concerned.

Subsequently, CPU 11 makes the operation device 33 execute the subtraction processing between the initial projection data 41 and the first differential data 47, whereby the n-th corrected projection data (in this case, n=1 and it is the first corrected projection data. The same is applied below.) 49 is generated (step 1053-1). The created first corrected projection data 49 contains an inverted component of an artifact component caused by the image reconstructing method (hereinafter referred to as inverted artifact component). In the step 1053-n, the subtraction processing between the initial projection data 41 and the first differential data may be executed after weighting processing called a well-known relaxation coefficient in the successive approximation processing technique is executed on the first differential data. Accordingly, the successive approximation processing can be early directed to convergence.

When the first corrected projection data 49 is created, CPU 11 makes the reconstruction calculating means 33a execute image reconstruction on the first corrected projection data 49 on the basis of a first corrected image reconstruction condition by the three-dimensional filtered back projection method, thereby forming an n-th corrected reconstructed image (in this case, n=1 and it is the first corrected reconstructed image. The same is applied below) 51 (step 1054-1). An artifact which occurs in the first corrected reconstructed image 51 and is caused by the image reconstructing method is offset by the inverted artifact component contained in the first corrected projection data 49, and the artifact is greatly reduced. Through the above processing, the first artifact removal processing is finished, and the first corrected reconstructed image 51 is displayed on the display device 35.

The first corrected image reconstruction condition used in the step 1054-1 is desired to be set so that the error of the re-projection processing is reduced on the assumption that the first corrected reconstructed image 51 is subsequently re-projected. For example, as for the first corrected image reconstruction condition, the reconstruction FOV and the center position of the reconstruction are determined so that the overall examinee is contained (for example, the maximum FOV size=500 mm, the reconstruction center position is the rotational center position of scanner). Furthermore, the reconstructed image matrix size, the reconstructed image slice number and the slice interval are set to be large so that the interpolation error at the re-projection time is reduced (for example, the image matrix size=1,024×1,024 pixels, the slice number=100 slices, the slice interval=0.5 mm). Furthermore, the reconstruction filter is determined so that the error between the re-projection data and the initial projection data is reduced (for example, ramp (Ramp) filter, shepp and logan (Shepp and Logan) filter is used).

The operator observes the first corrected reconstructed image 51 displayed on the display device 35, and determines whether it can be supplied for diagnosis again (step 106-n) (in this case, n=1 and thus step 106-1 is described. The same is applied below). When the operator determines that there is a risk that the first corrected reconstructed image 51 has many artifacts and thus it poses a problem for diagnosis (Yes of step 106-n), the first corrected reconstructed image 51 is subjected to the artifact removal processing operation again. When the operator determines that the artifacts do not pose a problem for diagnosis (No of step 106-n), a final reconstructed image (final image) described later is created. An input as to whether the artifact removal processing is necessary or not is executed in the same manner as the step 103.

When the operator inputs necessity of the artifact removal processing, the processing flow returns to the step 105-n again, and CPU 11 makes the operation device 33 execute second artifact removal processing (step 105-2). The operation device 33 which receives an instruction of executing the second artifact removal processing from CPU 11 re-projects the first corrected reconstructed image 51 along the X-ray beam or along the scan trajectory, thereby creating second re-projection data 53 (step 1051-2). This re-projection may be executed on all the first corrected reconstructed images 51, or executed on only images for which the operator determines that they contain many artifacts and thus pose a problem for diagnosis. The second re-projection data 53 created by the re-projection contain an artifact component which is not removed by the first artifact removal processing and appears in the first corrected reconstructed image 51.

When the second re-projection data 53 is created, the operation device 33 executes the differential calculation between the initial projection data 41 and the second re-projection data 53 to obtain second differential data 55 (step 1052-2). The second differential data 55 is an artifact component which is not removed by the first artifact removal processing and thus appears in the first corrected reconstructed image 51, and it is smaller as compared with the artifact component appearing in the initial reconstructed image 43.

Subsequently, in the operation device 33, the subtraction processing between the initial projection data 41 and the second differential data 55 is executed to create second corrected projection data 57 (step 1053-2). The created second corrected projection data 57 contains an inversed artifact component of the artifact component which is not removed by the first artifact removal processing and thus appears in the first corrected reconstructed image 51. In this step 1053-2, the second differential data 57 may be weighted and subtracted from the initial projection data 41.

The created second corrected projection data 57 is subjected to the image reconstruction by the three-dimensional filtered back projection method as in the case of the step 1054-1 in the reconstruction calculating means 33a, and a second corrected reconstructed image 59 is formed (step 1054-2). The second corrected reconstructed image 59 is more greatly reduced in artifact and thus nearer to a true image of the examinee as compared with the first corrected reconstructed image 51. Through this operation, the second artifact removal processing is finished, and the second corrected reconstructed image 59 is displayed on the display device 35.

The operator observes the second corrected reconstructed image 59 displayed on the display device 35, and determines whether it can be supplied for diagnosis again (step 106-2). When the operator determines that there is a risk that the second corrected reconstructed image 59 has many artifacts and thus it poses a problem for diagnosis (Yes of step 106-n), the processing returns to the step 105-n, and the artifact removal processing operation (creation of the n-th corrected reconstructed image) is repeated. When the operator determines that the artifact does not pose a problem for diagnosis (No of step 106), the operation of creating the final image is executed.

When the operator determines that the artifact does not pose any problem for diagnosis through the creation of the n-th corrected reconstructed image, the operator inputs an instruction of creating a final image to the operation unit (step 108). At this time, the operator inputs an image reconstruction condition of the final image (second image reconstruction condition) together with the input of the creating operation of the final image. The second image reconstruction condition is suitable for doctor's diagnosis of an examination site, and for example, there is used such a condition that the reconstruction FOV=250 mm, the reconstruction center position is deviated from the rotational center of scanner by 20 mm in x-direction and 10 mm in y-direction, the reconstruction matrix size=512×512 pixels, the number of slices=64 slices, the slice pitch=0.625 mm and the reconstruction filter is a filter for abdominal part.

When the operator instructs creation of the final image as described above, CPU 11 makes the operation device 33 execute the reconstruction calculation on the initial projection data 41 obtained in the step 101 or the n-th corrected projection data 49, 57, . . . obtained in the step 105-*n* under each set reconstruction condition, thereby creating a final image 61 (step 108).

As described above, the reconstruction condition in the successive approximation reconstruction processing step (the first image reconstruction condition) and the reconstruction condition when the final image is created (the second image reconstruction condition) are made different from each other, whereby an image under a desired condition can be obtained with high image quality.

The reconstructed final image 61 is displayed on the display screen of the display device 35 (step 109).

The first embodiment according to the invention is described above, however, various modifications may be made to the first embodiment. For example, in the first embodiment, the determination as to whether the artifact removal is necessary or not is performed on the basis of operator's determination. However, a threshold value may be set with respect to the total value or maximum value of the differential data between the initial projection data and the re-projection data in advance, and the steps 105-*n*, 106-*n* may be automatically repetitively executed until the differential data between the initial projection data and the re-projection data is not more than the threshold value. Accordingly, the operator is not required to make a determination as to whether the artifact removal processing is executed or not and input the determination result to the operation unit 3 on a case-by-case basis.

Figure 6:
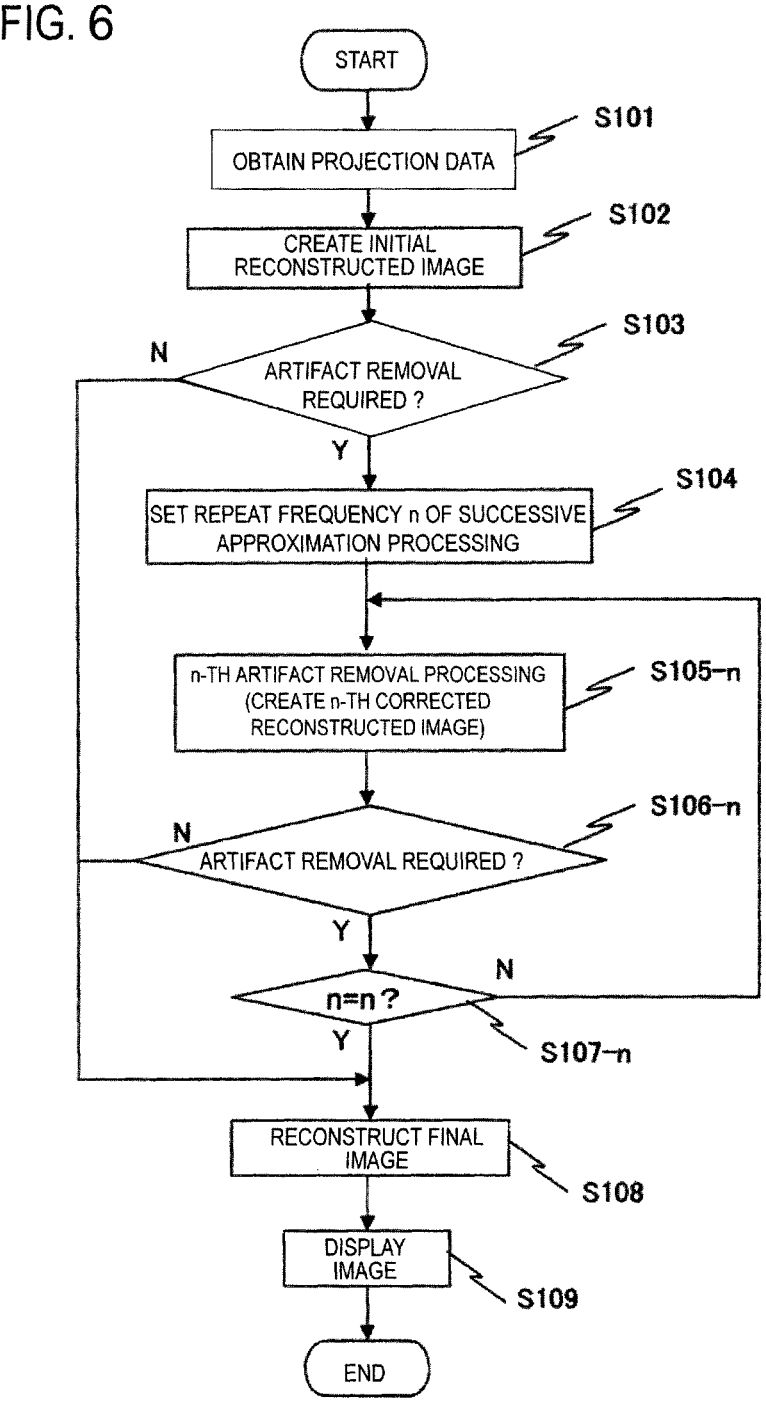
[FIG. 6] is a flowchart showing a modification of the first embodiment.

In the first embodiment, as shown in FIG. 6, the repeat frequency n of the steps 105-*n*, 106-*n* may be preset, and the final image may be reconstructed when the steps 105-*n*, 106-*n* are repeated at n times. Accordingly, the artifact removal can be finished within a predetermined time.

The repeat frequency n may be set in accordance with the cone angle or the slice position. That is, the repeat frequency n may be increased for an image at a large cone angle and a slice position at which a cone beam artifact appears strongly, and the repeat frequency n may be lowered for an image at a slice position at which the cone beam artifact does not appear so strongly, whereby the number of iterations of the successive approximation processing can be set to an optimum value. Accordingly, the time required to obtain a diagnosis image (final image) can be shortened.

SECOND EMBODIMENT

Next, a second embodiment of the invention will be described. In the second embodiment, the artifact removal processing is executed not by using the projection data of all the areas of the detector, but by using the projection data of a detector area corresponding to an area in which transmission data of the examinee is maximum (hereinafter referred to as effective detector range). A method of analyzing a reconstructed image, a sinogram or a scanogram to calculate or manually set the size of a circle containing the whole examinee and the center position of the circle is used as a method of determining a use range of projection data. In the second embodiment, the processing flow is basically identical to that shown in FIGS. 3 to 6. The second embodiment will be described hereunder by using a conceptual diagram of the artifact removal processing of the second embodiment shown in FIG. 7.

Figure 7:
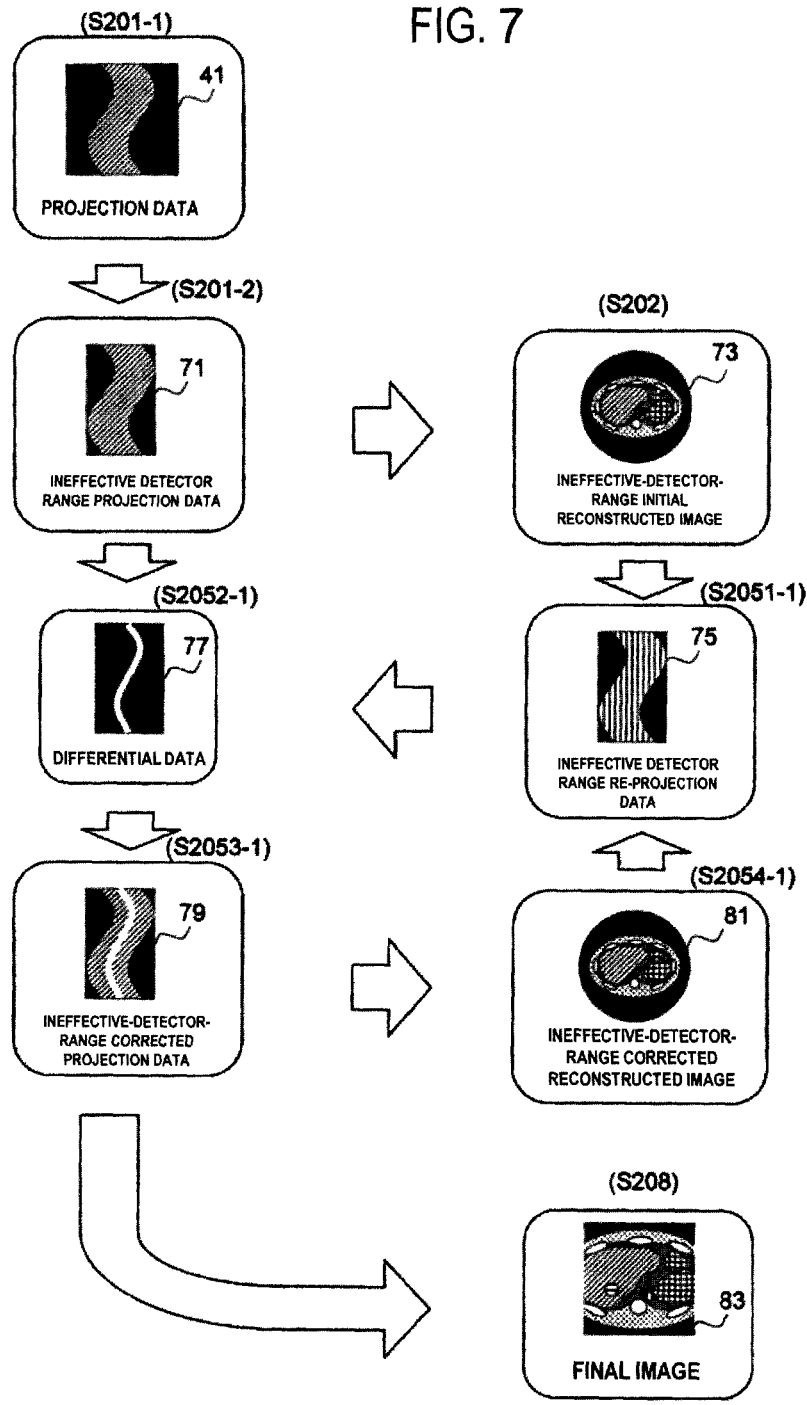
[FIG. 7] is a graphed diagram of the processing procedure of CT image formation according to a second embodiment of the invention.

As in the case of the first embodiment, CT scan of an examinee 24 is first performed to obtain initial projection data 41, and the initial projection data 41 is taken into the operation device 33 (step 201-1). The initial projection data 41 shown in FIG. 7 are shown as a pair of projection data, however, plural pairs of projection data are taken into the operation device 33.

Subsequently, an effective detector range is set by CPU 11 according to the method described above, the initial projection data existing in this effective detector range is extracted by the operation device 33, and ineffective-detector-range projection data 71 in which projection data out of the effective detector range are nullified are created (step 201-2).

With respect to the ineffective-detector-range re-projection data 71, the circle size is set to FOV, the circle center position is set to the center of the image reconstruction, and an ineffective-detector-range initial reconstruction image 73 is subjected to image reconstruction according to the three-dimensional filtered back projection method by the reconstruction calculating means 33*a* (step 202).

The operator observes the ineffective-detector-range initial reconstructed image 73 to determine whether the image of an examination site can be supplied for diagnosis, that is, whether artifact removal processing is executed or not, and inputs the determination result into the operation unit 3 by the input device 37. When the ineffective-detector-range initial reconstructed image 73 can be supplied for diagnosis, the artifact removal processing is not executed, and a final image is reconstructed. In the other case, the artifact removal processing is executed as follows.

According to the artifact removal processing, at a first time, the ineffective-detector range data of the ineffective detector-range initial reconstructed image 73 is re-projected as in the case of the first embodiment to create ineffective-detector-range first re-projection data 75 (step 2051-1). This ineffective-detector-range re-projection data 75 contains an artifact component when the ineffective-detector-range projection data 71 is subjected to image reconstruction.

Subsequently, the differential data between the ineffective-detector-range re-projection data 71 and the ineffective-detector-range re-projection data 75 is obtained by the operation device 33 (step 2052-1). This differential data 77 is an artifact component when the ineffective-detector-range projection data 71 is subjected to image reconstruction.

The differential data 77 obtained in the step 2052-1 is subtracted from the ineffective-detector-range re-projection data 75 to calculate ineffective-detector-range corrected projection data 79 (step 2053-1). This ineffective-detector-range corrected projection data 79 contains an inverted artifact component of the artifact component when the ineffective detector-range projection data 71 is subjected to image reconstruction. In this step 2053-1, the differential data 77 may be weighted and then subtracted from the ineffective-detector-range re-projection data 75 as in the case of the first embodiment.

Subsequently, as in the case of the first embodiment, the ineffective-detector-range corrected projection data 79 is subjected to image reconstruction by the three-dimensional filtered back projection method under the first image reconstruction condition to form an ineffective-detector-range corrected reconstructed image 81 (step 2054-1). The inverted artifact component is offset by the image reconstruction in the step 2054-1. However, the three-dimensional filtered back projection method itself is the approximation reconstruction method, and thus the artifact is not perfectly extinguished.

Therefore, the operator observes the ineffective-detector-range corrected reconstructed image 81 again to determine whether it can be supplied for diagnosis or not. When it is determined that the ineffective-detector-range corrected reconstructed image 81 cannot be supplied for diagnosis, execution of second artifact removal processing is input to the operation unit.

In the artifact removal processing, the calculation of the differential data between the re-projection data of the ineffective-detector-range corrected reconstructed image and the ineffective-detector-range initial projection data, the creation of the ineffective-detector-range n-th re-projection data and the image reconstruction of the ineffective-detector-range n-th re-projection data are repeated. When the operator determines that the reconstructed image of the ineffective-detector-range n-th re-projection data can be supplied for diagnosis, a final image 83 is reconstructed on the basis of the second image reconstruction condition (step 208).

The reconstructed final image 83 is displayed on the display device 35.

According to the second embodiment of the invention described above, the amount of data to be subjected to image reconstruction and re-projection may be small, and thus the time required for the artifact removal processing can be greatly reduced. Specifically, FOV containing an overall abdominal part of an adult having a large physical size is near to 500 mm, however, FOV of a child or a head portion is equal to about 200 mm. Therefore, the time required for the artifact removal processing is different between them by about two times.

THIRD EMBODIMENT

The embodiment of the invention is described above in detail. The invention is applicable to correction of image blurring in addition to the removal of the artifact occurring due to the image reconstructing method. That is, when a CT image is reconstructed, projection data cannot be created by only actually measured data, and thus there occurs a case where projection data must be created by interpolation to reconstruct an image. The interpolated projection data is created by interpolating the actually measured data and thus it contains a blurring component. A third embodiment also removes this blurring component contained in the interpolated projection data.

Figure 8:
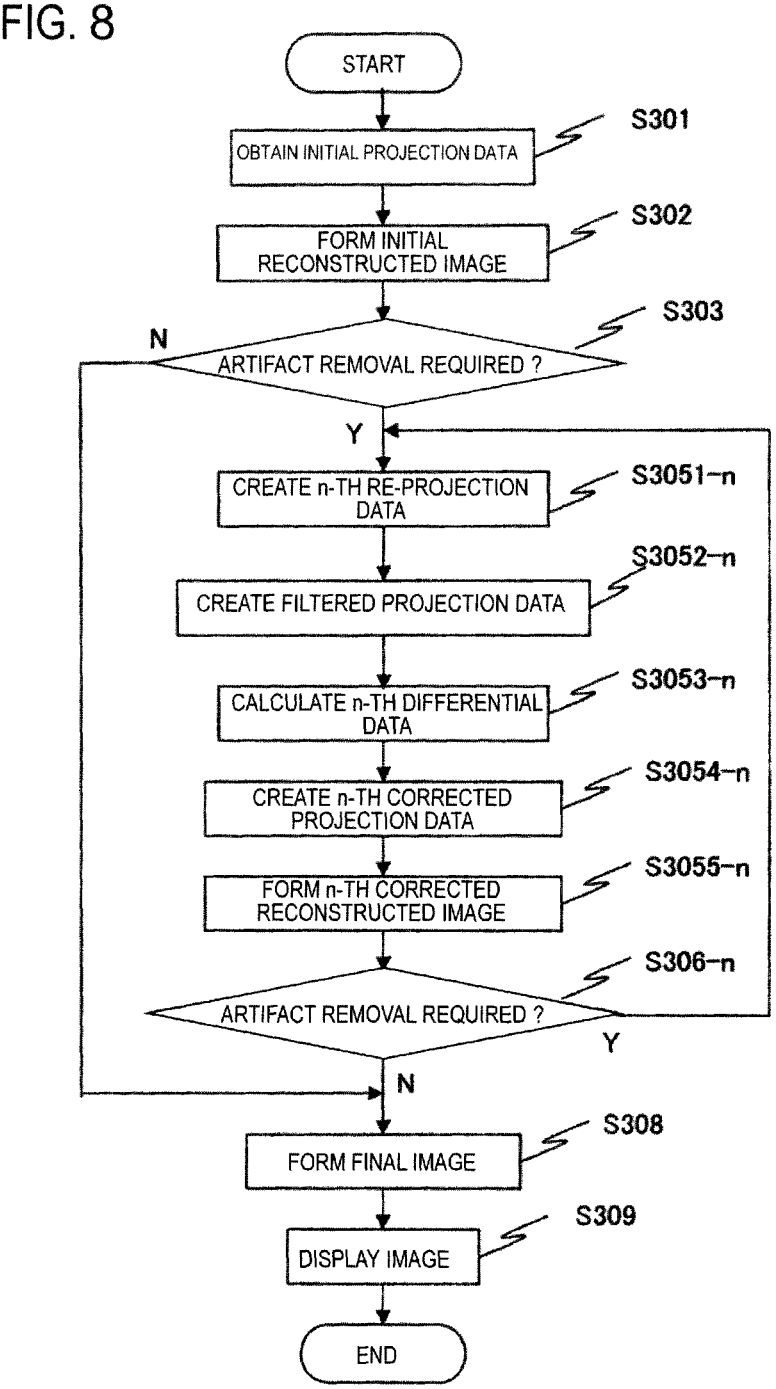
[FIG. 8] is a flowchart showing the processing procedure of CT image formation according to a third embodiment of the invention.

The third embodiment according to the invention will be described with reference to a flowchart shown in FIG. 8.

First, initial projection data are obtained by performing CT scan on an examinee 24 as in the case of the first and second embodiments (step 301).

Subsequently, initial projection data is subjected to image reconstruction on the basis of a first reconstruction condition set by an operator in the reconstruction calculating means 33a, thereby obtaining an initial reconstructed image (step 302).

The operator determines whether the initial reconstructed image is supplied for diagnosis or not, and inputs the determination result into the operation unit 3 (step 303). When the operator determines that the initial reconstructed image is supplied for diagnosis, a final image is reconstructed. When the initial reconstructed image has many artifacts caused by the image reconstructing method and thus cannot be supplied for diagnosis, the artifact removal processing is executed.

In the artifact removal processing, CPU 11 makes the operation device 33 create n-th re-projection data (step 3051-1). The creation of the re-projection data is executed by re-projecting the initial reconstructed image as in the case of the first and second embodiments, and it is necessary to create re-projection data by interpolation processing. Therefore, as compared with projection data obtained by imaging, the re-projection data becomes data containing blurring due to an effect of the interpolation processing. This blurring component poses a problem for the artifact removal processing.

Therefore, CPU 11 makes the operation device 33 execute filtering processing of adding, to the initial projection data, a blurring component equivalent to the blurring component contained in the first re-projection data, thereby creating filtered projection data (step 3052-1). A filter function used for the filtering processing can be determined by imaging and re-projecting a small structure such as a minute spherical body or a slender cylindrical body. The filtering processing adding, to the initial projection data, the blurring component may be executed before the difference between first re-projection data and filtered projection data described next is calculated.

Subsequently, CPU 11 makes the operation device 33 execute the differential calculation between the first re-projection data and the filtered projection data, thereby calculating the differential data between the first re-projection data and the filtered projection data (step 3053-1). The differential calculation in this step 3053-1 offsets the blurring components contained in both the first re-projection data and the filtered projection data. Accordingly, the calculated differential data becomes an artifact component caused by the image reconstructing method when the initial projection data is reconstructed.

The calculated differential data is subtracted from the initial projection data, so that the first corrected projection data is created (step 3054-1). The first corrected projection data obtained by subtracting the differential data from the initial projection data contains an inverted component of an artifact caused by the image reconstructing method when the first corrected projection data is subjected to the image reconstruction by the three-dimensional filtered back projection method. In this step 3054-1, the subtraction processing may be executed between the differential data and the initial projection data after the differential data is weighted as in the case of the first and second embodiments.

The first corrected projection data created in step 3054-1 is subjected to image reconstruction on the basis of the first image reconstruction condition, thereby forming a first corrected reconstructed image (step 3055-1). The first corrected reconstructed image is displayed on the display device 35. The first corrected reconstructed image obtained in this step is obtained by reconstructing the first corrected projection data containing the inverted component of the artifact caused by the image reconstructing method, and the artifact caused by the image reconstructing method is greatly reduced.

On the basis of the image observation result of the operator, the calculation of the n-th differential data based on the initial projection data 41 and the re-projection data of the n-th corrected reconstructed image (n means the n-th artifact removal processing), the creation of the n-th corrected projection data based on the subtraction between the initial projection data and the n-th differential data and the successive approximation processing (recursion processing) of repeating formation of the n-th corrected reconstructed image based on the image reconstruction of the n-th corrected projection data and the display on the image display device 35 are executed from n=2 till n=n (with respect to n=1, these processing has been executed as the first time by the step 3055-1).

When the operator determines that the n-th corrected reconstructed image can be supplied for diagnosis and inputs it to the operation unit 3 that (n+1)-th artifact removal processing is unnecessary, CPU 11 stops the successive approximation processing, and makes the reconstruction calculating means 33a execute the image reconstruction on the n-th corrected projection data under the second image reconstruction condition, thereby obtaining a final image (step 308).

The obtained final image is displayed on the screen of the image display device 35 (step 309), stored into the storage device 39 provided to the operation unit 3 and supplied for doctor's image diagnosis.

The third embodiment of the invention described above can exclude the influence of the blurring component occurring in the process of re-projection (back projection) of the reconstructed image which is performed to remove the artifact caused by the image reconstructing method.

The invention is described above on the basis of the first to third embodiments. However, the invention is not limited to the above embodiments, and various modifications may be made without departing from the subject matter of the invention. For example, in the above embodiments, the final image is reconstructed on the basis of the second image reconstruction condition when the effect of the artifact on the diagnosis is reduced, however, it may be performed as occasion demands. That is, when an examination site can be diagnosed on the basis of an n-th corrected reconstructed image, it is unnecessary to obtain a high-precision final image.

Furthermore, when imaging data obtained by normal scan under which the bed is not moved is re-constructed by the Feldkamp method during the imaging operation of the multi-slice CT having a broad cone angle, the reconstructed FOV range has a shape like a bead of an abacus at a position which is far away from a mid plane (the cross-section at the center portion in the slice direction). When the reconstructed data at such a position is re-projected, the obtained re-projection data lacks some data and thus becomes incomplete as compared with the initial projection data. When the incomplete re-projection data and the initial projection data are compared with each other, a large error occurs, and thus it greatly adversely affects the obtained final image.

In such a case, a countermeasure may be taken by expanding the reconstructed image data in the successive approximation processing in the reconstruction slice direction, expanding the detector size in the re-projection process in the slice direction or compensating the incomplete data range in the re-projection process with the projection data. Specifically, with respect to the expansion in the slice direction, a virtual image slice is disposed out of the image range of the initial reconstructed image or a virtual detector is disposed out of the detector range under imaging. Furthermore, with respect to the compensation based on the projection data, substitute or weighted addition based on projection data is performed. As described above, by the expansion of the slice-direction range or the compensation based on the projection data, a data-missing portion is corrected, so that an excellent image is obtained even in the normal scan of the multi-slice CT.

DESCRIPTION OF REFERENCE NUMERALS

1 scanner, 2 bed, 3 operation unit, 11 central control device (CPU), 27 X-ray detector, 33 operation device, 33a reconstruction calculating means, 41 initial projection data, 43 initial reconstructed image, 45, 53 re-projection data, 47, 55 differential data, 49, 57 corrected projection data, 51, 59 corrected reconstructed image, 61 final image, 71 ineffective-detector-range projection data, 73 ineffective-detector-range initial reconstructed image, 75 ineffective-detector-range re-projection data, 77 differential data, 79 ineffective-detector-range corrected projection data, 83 final image

The invention claimed is:

1. An X-ray CT image forming method that obtains a reconstructed image of an examination site of an examinee by executing image reconstruction on projection data obtained by CT scan, characterized by comprising:
   (1) a step of executing image reconstruction on the projection data to obtain an initial reconstructed image;
   (2) a step of re-projecting the initial reconstructed image to obtain re-projection data;
   (3) a step of obtaining differential data between the projection data and the re-projection data;
   (4) a step of subtracting the differential data from the projection data to obtain corrected projection data containing an inverted artifact component; and
   (5) a step of executing image reconstruction on the corrected projection data to obtain a corrected reconstructed image.

2. The X-ray CT image forming method according to claim 1, wherein subsequently to the step (5), the initial reconstructed image of the step (2) is replaced by the corrected reconstructed image obtained in the step (5), and the steps from (2) to (5) are repeated at n times (n represents an integer of n≥1).

3. The X-ray CT image forming method according to claim 2, wherein an upper limit is set to n.

4. An X-ray CT apparatus in which an X-ray source and an X-ray detector are disposed to face each other and sandwich an examinee therebetween and projection data obtained by executing CT scan on the examinee are reconstructed by an image processing device to obtain a reconstructed image of an examination site of the examinee, characterized in that the image processing device comprises:
   artifact component extracting means that extracts an artifact component caused by executing image reconstruction based on the projection data;
   corrected projection data creating means that creates corrected projection data containing an inverted artifact component by subtracting the artifact component from the projection data; and
   corrected reconstructed image creating means that executes image reconstruction of a corrected reconstructed image in which the artifact is reduced by using the corrected projection data containing the inverted artifact component,
   wherein the image processing device comprises successive approximation image reconstructing means that makes the artifact component extracting means re-project the corrected reconstructed image created by the corrected reconstructed image creating means again to obtain n-th re-projection data and then obtain n-th differential data between the projection data and the n-th re-projection data, makes the corrected projection data creating means subtract the n-th differential data from the projection data to obtain n-th corrected projection data, and makes the corrected reconstructed image creating means repetitively execute an operation of reconstructing the n-th corrected projection data from n=1 till n=n wherein n represents an integer to obtain a corrected reconstructed image in which the artifact diminishes gradually.

5. The X-ray CT apparatus according to claim 4, wherein the artifact component extracting means comprises means that re-projects the reconstructed image obtained by reconstructing the projection data to obtain re-projection data, and means that obtains differential data between the projection data and the re-projection data.

6. The X-ray CT apparatus according to claim 4, wherein an upper limit value of the repeat frequency n is set before image reconstruction processing.

7. The X-ray CT apparatus according to claim 4, wherein input means for inputting repetition of obtaining the corrected reconstructed image on a case-by-case basis is provided to an operation unit.

8. The X-ray CT apparatus according to claim 4, wherein the X-ray detector is a multi-slice type X-ray detector, and the image reconstructing method belongs to a filtered back projection method.

9. The X-ray CT image forming method according to claim 1, wherein:
- the re-projection data is obtained in the step (2) by re-projecting the initial reconstructed image while applying interpolation processing,
- filtered projection data is created prior to step (3) by executing filtering processing of adding a blurring component contained in the re-projection data to the projection data; and
- the differential data is obtained in the step (4) between the filtered projection data and the re-projection data.

* * * * *